United States Patent [19]
Robson et al.

[11] Patent Number: 5,848,714
[45] Date of Patent: Dec. 15, 1998

[54] SUTURE RACK

[75] Inventors: David C. Robson, Providence, R.I.; Larry Travers, Westport; Quinton J. Farrar, Lakeville, both of Mass.

[73] Assignee: Deknatel Technology Corporation, Wilmington, Del.

[21] Appl. No.: 772,488

[22] Filed: Dec. 23, 1996

[51] Int. Cl.⁶ ........................................... A47F 7/00
[52] U.S. Cl. .................... 211/170; 211/126.3; 211/85.13; 206/63.3
[58] Field of Search ................................ 211/170, 169.1, 211/175, 47, 126.2, 126.3, 85.13; 206/63.3, 365, 370, 558, 565

[56] References Cited

U.S. PATENT DOCUMENTS

| | | | |
|---|---|---|---|
| D. 272,600 | 2/1984 | Kubas | D9/346 |
| 2,281,236 | 4/1942 | Eckman . | |
| 3,363,751 | 1/1968 | Shave et al. | 206/63.3 |
| 3,444,994 | 5/1969 | Shave | 206/63.3 |
| 3,556,620 | 1/1971 | Gutierrez | 211/170 X |
| 3,834,778 | 9/1974 | Morrison et al. | 211/126.3 X |
| 3,857,482 | 12/1974 | Shelton . | |
| 4,261,463 | 4/1981 | Shave | 206/63.3 |
| 4,480,745 | 11/1984 | Loge et al. | 211/126.3 X |
| 4,505,395 | 3/1985 | Nathan | 211/126.3 |
| 4,708,241 | 11/1987 | Black | 206/63.3 |
| 4,896,767 | 1/1990 | Pinheiro | 206/63.3 |
| 5,282,533 | 2/1994 | Holzwarth et al. | 206/63.3 |
| 5,312,250 | 5/1994 | Ellman et al. | 206/379 X |
| 5,335,775 | 8/1994 | Scanlon et al. | 206/63.3 |
| 5,662,228 | 9/1997 | Mendoza et al. | 211/169.1 X |

FOREIGN PATENT DOCUMENTS

| | | |
|---|---|---|
| 0 498 460 A1 | 8/1992 | European Pat. Off. . |
| WO 95/08302 | 3/1995 | WIPO . |
| PCT/US97/ 21988 | 3/1998 | WIPO . |

OTHER PUBLICATIONS

USSC Sutures, E–Pack* Procedure Kit.
Deknatel, "Wound Closure Cardiovascular Products" 1992.

*Primary Examiner*—Robert W. Gibson, Jr.
*Attorney, Agent, or Firm*—Fish & Richardson P.C.

[57] ABSTRACT

A rack for holding a surgical suture includes a first base having a base connector that can releasably engage a mating base connector of a second base. The rack includes a tray attached to the first base for rotation with respect to the first base. The tray has at least one suture-holding section with resilient clips and bosses to retain a surgical sutures in the suture-holding section. The tray has a pin which defines a rotatable axis and the first base has a connector that engages the pin for releasably connecting the tray to the first base. An array of suture-holding racks includes a first rack having a base with a base connector engaging a mating base connector of a base of a second rack. The first base can be attached to up to four adjacent bases.

31 Claims, 6 Drawing Sheets

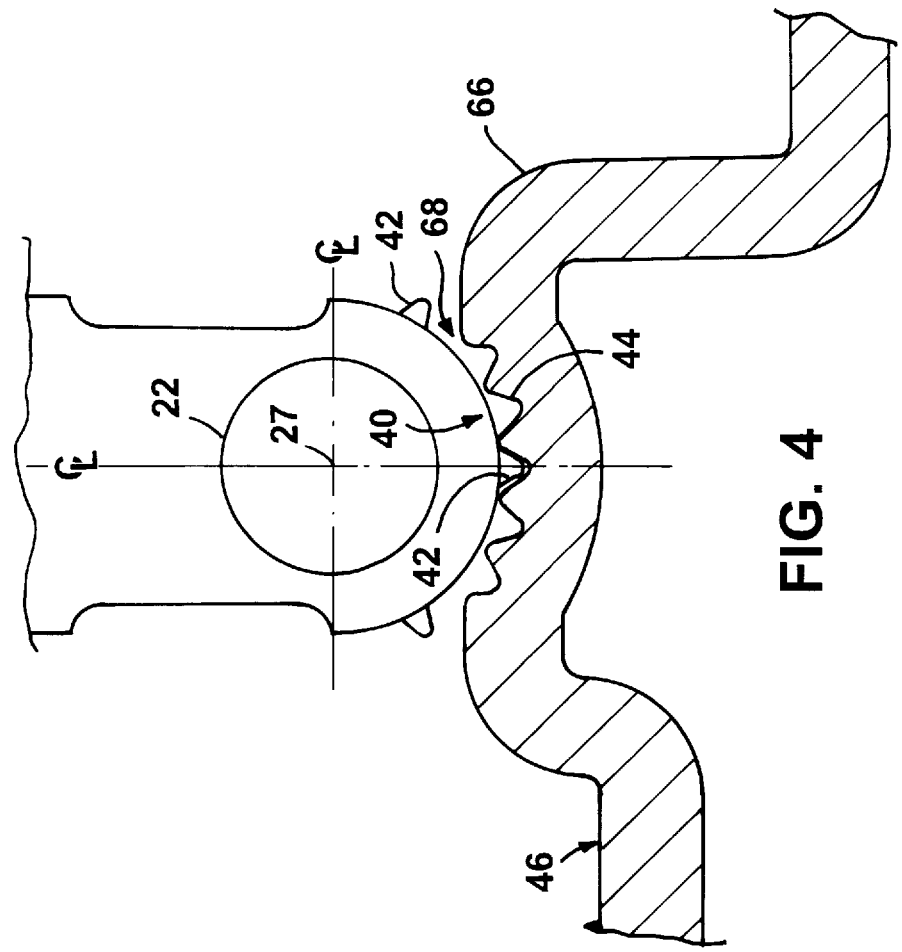
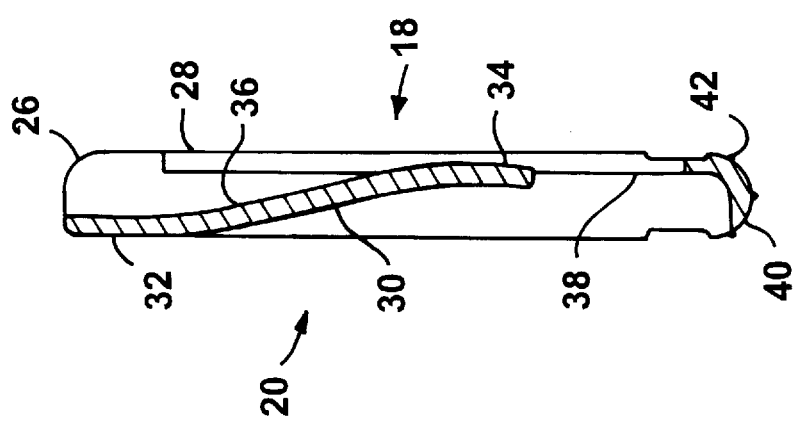
FIG. 4
FIG. 3

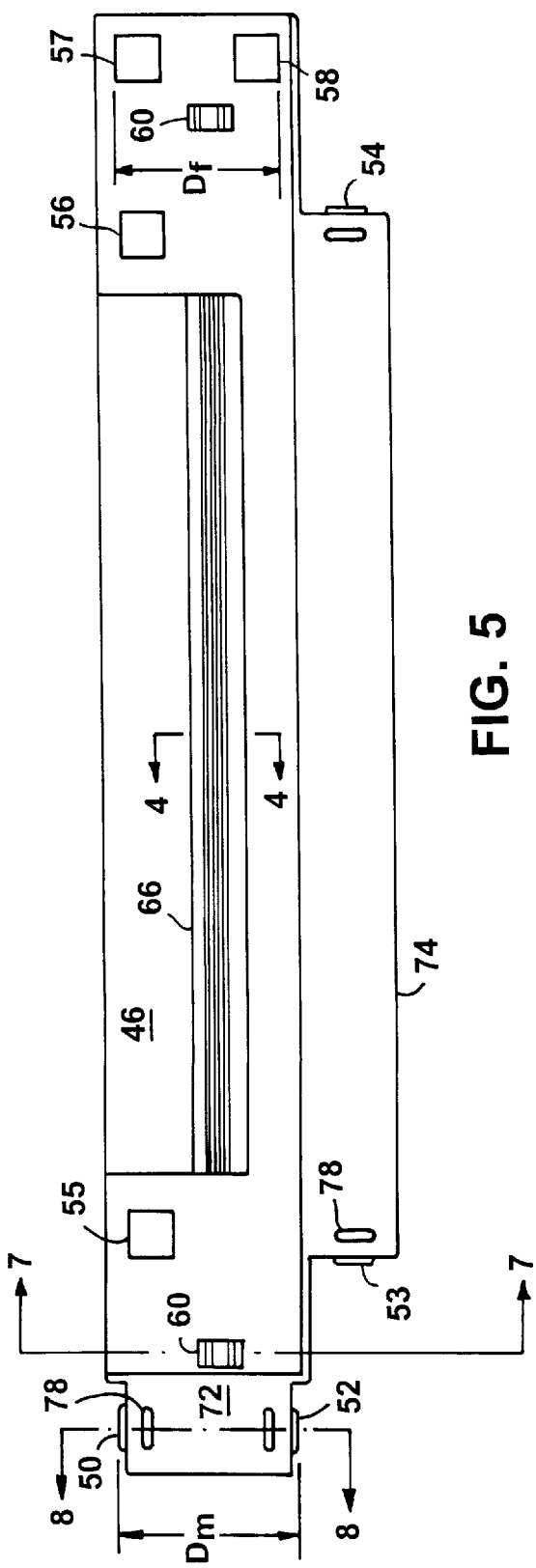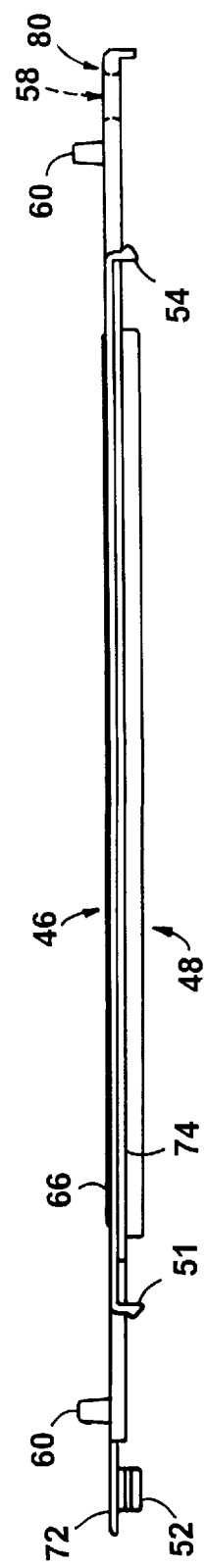

SUTURE RACK

BACKGROUND OF THE INVENTION

This invention relates to racks for holding and displaying surgical sutures.

Sutures are commonly provided in individually sterilized and prepackaged envelopes. Different kinds of sutures are available to meet the specific needs of a procedure. It is common for a physician to use several different types of sutures during a procedure, and thus a variety of sutures is generally kept close at hand.

SUMMARY OF THE INVENTION

The invention features a rack for holding a surgical suture. The rack includes a first base having a base connector that can releasably engage a mating base connector of a second base, and a tray attached to the first base. The tray has at least one suture-holding section.

Preferred embodiments have multiple base connectors on the first base arranged to engage mating base connectors on each of a second, third, fourth and fifth base. The tray is attached to the first base for rotation with respect to the first base through an angle of about 180 degrees. A tray-holding mechanism retains the tray in a selected rotated position. The tray-holding mechanism preferably includes an outwardly projecting knob on the tray and a detent on the base. The detent is alignable with the knob to retain the tray in a rotated position. The tray has a pin which defines a rotatable axis. The first base has a connector that engages the pin for releasably connecting the tray to the first base.

A resilient clip retains the surgical suture in the suture-holding section. The tray has a boss for engaging a corresponding recess in a suture package to retain the suture package in the suture-holding section. A packaged suture is positioned in the suture-holding section. The tray includes multiple suture-holding sections each containing a packaged suture.

The rack includes an unsealed packaged suture positioned in the suture-holding section and a sterile package surrounding the rack.

According to another aspect of the invention, an array of suture-holding racks includes a first rack having a first base with a base connector engaging a mating base connector of a second base. The first base can be attached to up to four adjacent bases.

In another aspect, the invention features a sterile packaged suture assembly including a tray for attachment to a first base of a rack for holding surgical sutures, wherein the first base has a base connector that can releasably engage a mating base connector of a second base. The tray includes a suture-holding section and an unsealed packaged suture positioned within said suture-holding section. A sterile package surrounds the tray.

According to another aspect of the invention, a method of interconnecting suture holding racks includes providing a plurality of racks each having a base with multiple base connectors and interconnecting the racks by mating the base connectors of adjacent racks.

According to another aspect of the invention, a method of interchanging suture holding trays includes providing a base including a connector for releasably attaching a tray to the base; releasably attaching a first tray to the base, the first tray including a first suture-holding section; and removing the first tray from the base and attaching a second tray to the base, the second tray including a second suture-holding section.

The rack of the invention can advantageously keep several prepackaged sutures close at hand during a surgical procedure. The rack is enclosed in a single sterile package such that the sutures in the rack are accessible and ready for use simply by removing the sterile package. Sutures can be removed from their individual packages without the need for handling the suture package. The trays of the racks can be easily interchanged to accommodate different sizes of suture packages. The trays can also be rotated out of the way or to display sutures in other racks. The bases of the racks can be conveniently interconnected to form an organized array of suture-holding racks.

Other features and advantages will be apparent from the following description and from the claims.

BRIEF DESCRIPTION OF THE DRAWINGS

FIG. 3 is a cross-sectional view of the tray, taken along lines 3—3 in FIG. 2;

FIG. 4 is an enlarged fragmentary end view of the tray, shown in a mating position with a cross-sectional view of the base, taken along lines 4—4 in FIG. 5;

FIG. 5 is a plan view of a base of a suture-holding rack of FIG. 1;

FIG. 6 is a side elevation view of the base of FIG. 5;

DESCRIPTION OF THE PREFERRED EMBODIMENTS

Figure 1:
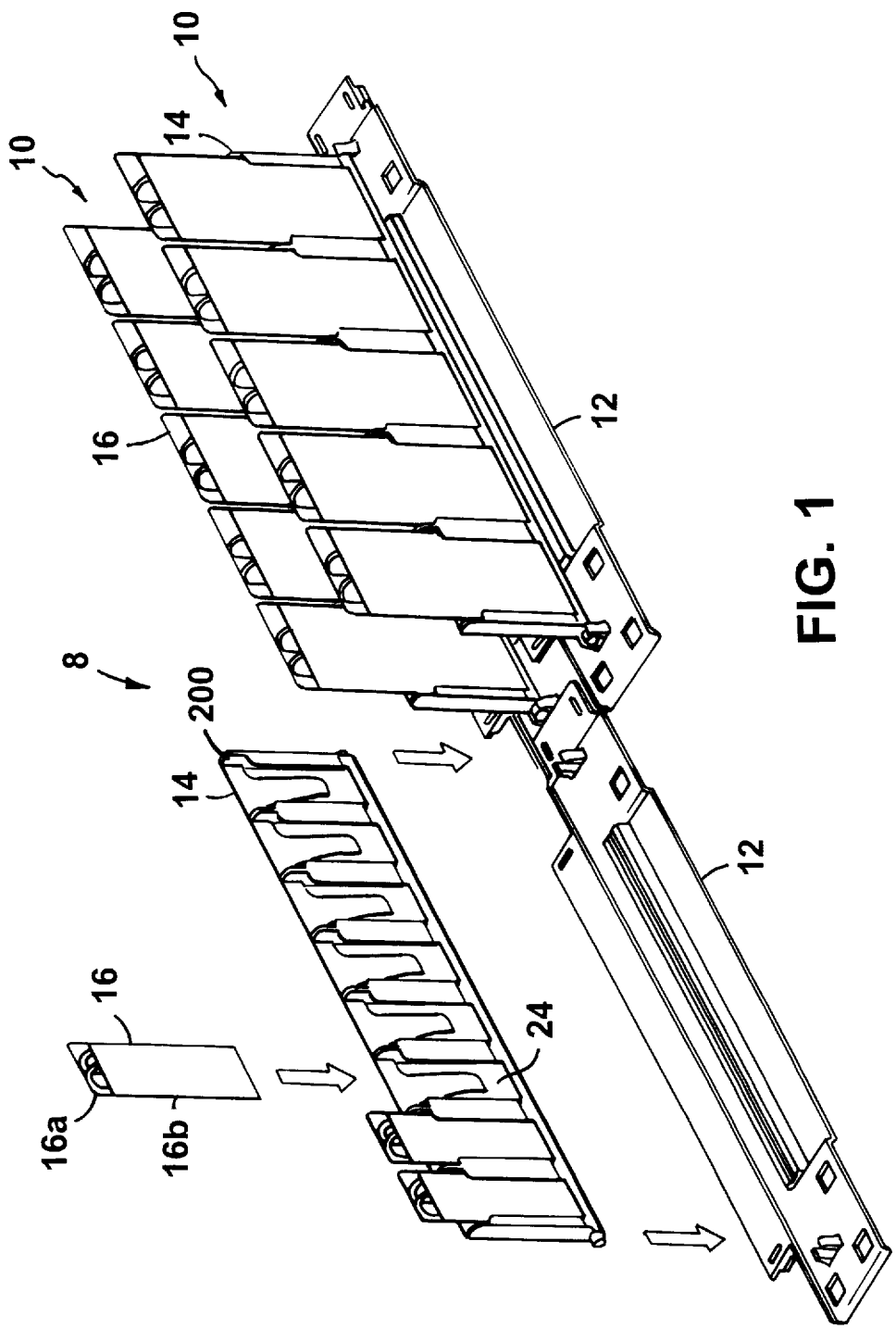
FIG. 1 is a diagrammatic representation of an array of suture-holding racks, according to the invention.

FIG. 1 illustrates an array 8 of interconnected suture-holding racks 10. Each rack 10 includes a base 12 and a releasably connected tray 14. The bases 12 of racks 10 are interconnectable (described further below) to form array 8. Tray 14 includes suture-holding compartments 24 for holding packaged sutures 16. Packages sutures 16 each include a suture package 16a containing a suture 16b.

Figure 2:
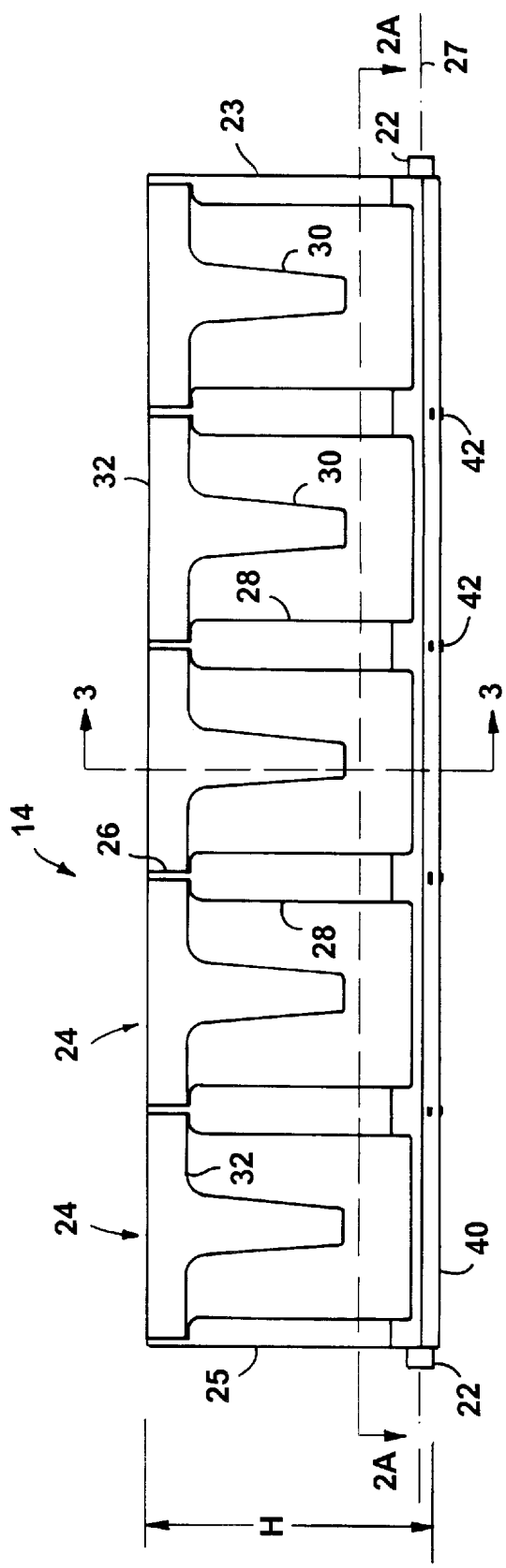
FIG. 2 is a side elevation view of a tray of a suture-holding rack of FIG. 1.
Figure 2A:
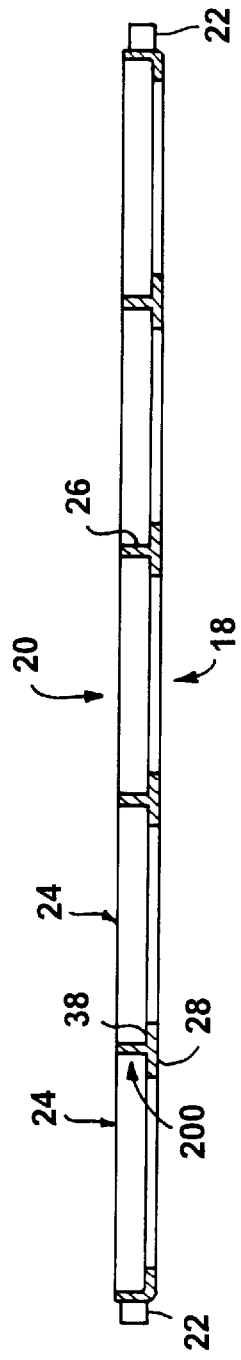
FIG. 2A is a cross-sectional view of the tray, taken along lines 2A—2A in FIG. 2.

Referring to FIGS. 2 and 2A, tray 14 has two integrally molded, outwardly extending pins 22, one at each end 23 and 25, that define an axis of rotation 27. Several suture-holding compartments 24, here five being shown, are each separated by an integral wall 26 extending along the height H of tray 14. Flanges 28 extend from wall 26 define slots 200 to help retain packaged sutures 16 within compartments 24. Between flanges 28, the front side 18 of each compartment 24 is substantially open, enabling descriptions on the front of the suture packaging to be displayed.

Referring also to FIG. 3, a rail portion 32 of tray 14 extends along back side 20 of tray 14 and is connected to walls 26. A retaining clip 30, in the form of a cantilevered, resilient finger, extends downward into each compartment 24 from rail 32. Each clip 30 projects from rail 32 toward front side 18 of tray 14, with a free end 34 curved back slightly toward back side 20 of tray 14. A front face 36 of each clip 30 presents a smooth surface to the packaged suture 16 as the suture is slidingly inserted into and removed from compartment 24. As a packaged suture 16 is inserted into compartment 24, clip 30 is displaced rearward and acts as a cyclable leaf spring to exert pressure against packaged suture 16 to secure it against inner surfaces 38 of flanges 28. In use, resilient clip 30 and flanges 28 retain the suture package while the surgeon removes the suture from the package.

Referring to FIG. 4, a bottom surface 40 of tray 14 has a circular arc shape which is concentric about pins 22. Bottom surface 40 includes outwardly facing projections 42 (here three are shown) at multiple locations along the length of tray 14 (see FIG. 2). Pins 22 and projections 42 are used to connect tray 14 to base 12 and to hold tray 14 in a desired orientation.

Referring to FIGS. 5 and 6, base 12 has a top face 46; tray connectors 60 extending upward from top face 46 of base 12 to engage pins 22 of tray 14 to releasably secure tray 14 against base 12; and male base connectors 50, 52, 53 and 54, and female base connectors 55, 56, 57 and 58 for releasably connecting base 12 to adjacent bases 12. An elevated support rib 66 located between the two tray connectors 60 supports bottom surface 40 of secured tray 14.

Figure 7:
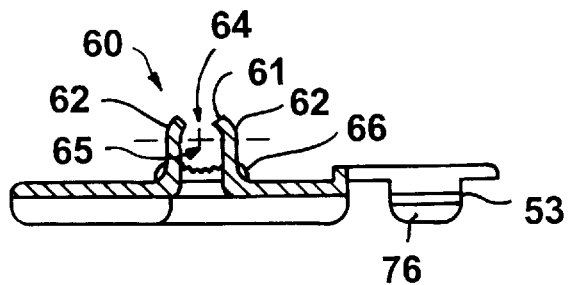
FIGS. 7 is a cross-sectional view of the base, taken along lines 7—7 in FIG. 5.

Referring to FIG. 7, each tray connector 60 has two facing cantilevered arms 62, with ends 61 of each arm 62 curved toward each other. Ends 61 define a restriction 64 through which pin 22 of the tray snap-fits into an aperture 65 during assembly of tray 14 to base 12 to secure tray 14 to base 12 while enabling pin 22 to rotate within tray connector 60.

Referring again to FIG. 4, to hold tray 14 in a desired orientation, a curved upper surface 68 of support rib 66 includes a series of longitudinal recesses 44 extended along the length of support rib 66. At least one projection 42 of tray 14 engages a recess 44 to lock tray 14 to base 12 at a desired orientation. Rib 66 is positioned above top face 46 of base 12 enabling tray 14 to be rotated over an angle of 180 degrees about axis 27 such that tray 14 can lie flat. Tray 14 is constructed to resiliently flex to disengage projections 42 from recesses 44 to enable tray 14 to be rotated to a desired position.

Figure 8:
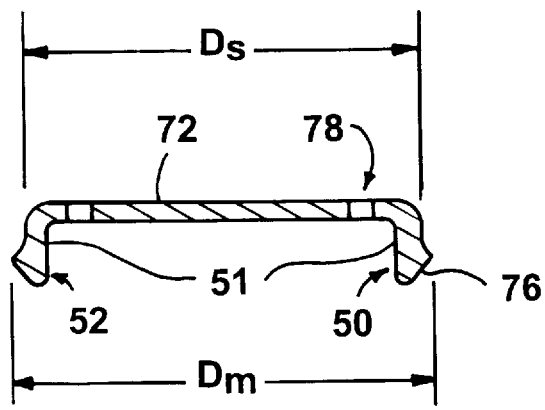
FIG. 8 is a cross-sectional view of the base, taken along lines 8—8 in FIG. 5.

Referring to FIGS. 5 and 8, male connectors 50, 52, 53 and 54 include fingers 51 extending downward from raised platforms 72 and 74 which engage a mating female connector 57, 58, 55 and 56, respectively, to secure a first base 12 to adjacent bases 12. Female connectors 55, 56, 57 and 58 are holes extending through base 12. The arrangement of the pairs of male/female connectors enables base 12 to be attached to up to four additional bases 12 (see FIG. 1). When bases 12 are so connected, raised platform 72 or 74 of the bases providing the male connectors at any given connection overlaps upper face 46 of the base providing the female connectors. The releasable connection of trays 14 to bases 12 permit an empty tray to be quickly replaced with a new tray without the necessity of removing the associated base from an array of racks.

The distance $D_m$ between cam surfaces 76 of fingers 51 of a male connector is greater than the distance $D_f$ between the outer edges of a mating female connector enabling fingers 51 of the male connector to resiliently deflect during engagement. Holes 78 through platforms 72 and 74 adjacent the male connectors decrease the torsional rigidity of platforms 72, 74 to aid in the deflection of fingers 51 during engagement. A radius 80 (FIG. 6) at the upper edge of the holes of the female connector helps to align fingers 51 of the male connector prior to engagement.

Figure 9:
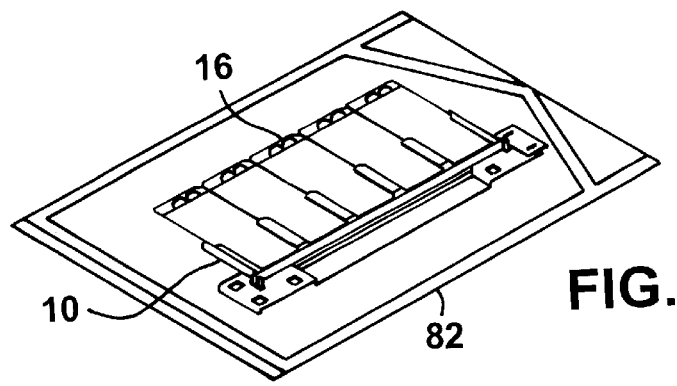
FIG. 9 is a diagrammatic illustration of a loaded rack enclosed in sterile packaging, according to the invention.

Referring to FIG. 9, rack 10 is preferably supplied to the customer preassembled in sterile packaging 82 with packaged sutures 16 pre-loaded. Sterile rack packaging 82 allows packaged sutures 16 to be supplied unsealed, i.e., not in individual sterile packaging, thus enabling the sutures to be made accessible and ready for use simply by removing the rack from packaging 82. Alternatively, tray 14 with unsealed, pre-loaded sutures 16 can be supplied in sterile packaging 82 without base 14.

Tray 14 may be configured with seven or eight suture-holding sections 24 to accommodate small suture packages 16, with five suture-holding sections 24 to accommodate large suture packages 16, or with four suture-holding sections 24 to accommodate absorbable sutures in foil carrier packaging. The number and size of suture-holding sections 24 in each tray 14 may vary within array 8, as illustrated in FIG. 1. Compatible suture package sizes include, for example, DSP Worldwide, Inc. packaged sutures 3-810W, X-5904, and B4120N.

Other embodiments are within the scope of the following claims.

Figure 10:
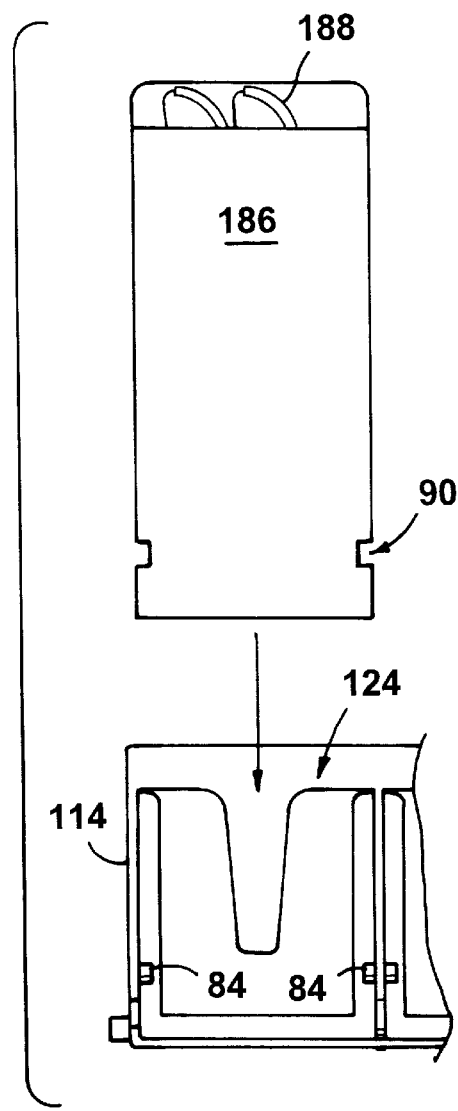
FIG. 10 is a fragmentary view of tray with a packaged suture according to an additional embodiment of the invention.
Figure 11:
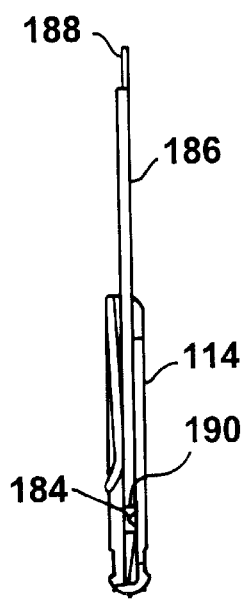
FIG. 11 is a side view showing the packaged suture of FIG. 10 positioned in the tray.

For example, referring to FIG. 10, suture holding section 124 of tray 114 includes bosses 84 and suture package 186 includes corresponding recesses 90, e.g., notches, which engage bosses 84 when suture package 186 is placed in suture holding section 124 (see FIG. 11). The engagement of recesses 90 and bosses 84 helps retain suture package 186 within suture holding section 124 while a surgeon is removing an associated suture 188.

What is claimed is:

1. A rack for holding a surgical suture, comprising:
   a first base having a base connector that can releasably engage a mating base connector of a second base, and
   a tray attached to the first base, said tray including a suture-holding section having a flange defining a slot for receiving a flat envelope containing a surgical suture.

2. The rack of claim 1 wherein the first base includes a plurality of base connectors arranged to engage mating base connectors on each of a second, third, fourth and fifth base.

3. The rack of claim 1 wherein the tray is attached to the first base for rotation with respect to the first base through an angle of about 180 degrees.

4. The rack of claim 3 further comprising a tray-holder that retains the tray in a selected rotated position.

5. The rack of claim 4 wherein the tray-holder comprises an outwardly projecting knob on the tray and a detent on the first base, the detent being alignable with the knob to retain the tray in a rotated position.

6. The rack of claim 1 wherein the tray further comprises a pin which defines a rotatable axis, and the first base comprises an upstanding tray connector that engages the pin for releasably connecting the tray to the first base.

7. The rack of claim 1 wherein the tray further comprises a resilient clip for retaining a surgical suture in the suture-holding section.

8. The rack of claim 7 further comprising a suture-retaining boss.

9. The rack of claim 1 wherein the tray further comprises a boss for engaging a corresponding recess in a suture package to retain said suture package in the suture-holding section.

10. The rack of claim 1 further including a packaged suture positioned in the suture-holding section.

11. The rack of claim 1 wherein the tray further comprises multiple suture-holding sections.

12. The rack of claim 11 further including multiple packaged sutures, each of the multiple packaged sutures being located within a corresponding suture holding section.

13. The rack of claim 1 further including an unsealed packaged suture positioned in the suture-holding section and a sterile package surrounding said rack.

14. A rack for holding surgical sutures, comprising:
a first base having a base connector that can releasably engage a mating base connector of a second base and a detent, and
a tray attached to the first base for rotation with respect to the first base, the tray including a suture-holding section with a resilient clip to retain a surgical suture in the suture-holding section, and a knob aligned with the detent to retain the tray in a selected rotated position.

15. The rack of claim 14 wherein the first base includes a plurality of base connectors arranged to engage mating base connectors on each of a second, third, fourth and fifth base.

16. The rack of claim 14 further including a packaged suture positioned in the suture-holding section.

17. An array of suture-holding racks, comprising:
a first rack for holding a surgical suture, said first rack including
a first base having a base connector engaging a mating base connector of a second base, and
a first tray attached to the first base, the first tray including a first suture-holding section having a flange defining a slot for receiving a flat envelope containing a surgical suture, and
a second rack for holding a surgical suture, said second rack including
the second base having the mating base connector engaging the base connector of the first base, and
a second tray attached to the second base, the second tray including a second suture-holding section having a flange defining a slot for receiving a flat envelope containing a surgical suture.

18. The rack of claim 17 wherein the first base includes a plurality of base connectors engaging mating base connectors on each of a third, fourth and fifth base.

19. A sterile packaged suture assembly, comprising:
a tray for attachment to a first base of a rack for holding surgical sutures, wherein the first base has a base connector that can releasably engage a mating base connector of a second base, said tray including a suture-holding section and an unsealed packaged suture positioned within said suture-holding section, and
a sterile package surrounding said tray.

20. A method of interconnecting suture holding racks, comprising:
providing a plurality of racks each having
a base with multiple base connectors, and
a tray attached to the base and including a suture-holding section having a flange defining a slot for receiving a flat envelope containing a surgical suture, and
interconnecting the racks by mating the base connectors of adjacent racks.

21. A method of interchanging suture holding trays, comprising:
providing a base including a connector for releasably attaching a tray to the base, the connector defining an aperture,
releasably attaching a first tray to the base by inserting a corresponding pin of the tray into the aperture, the first tray including a first suture-holding section, and
removing the first tray from the base and attaching a second tray to the base by inserting a corresponding pin of the second tray into the aperture, the second tray including a second suture-holding section.

22. A rack for holding a surgical suture, comprising:
a first base having a base connector that can releasably engage a mating base connector of a second base, and
a tray attached to the first base for rotation with respect to the first base through an angle of about 180 degrees, said tray including a suture-holding section.

23. The rack of claim 22 further comprising a tray-holder that retains the tray in a selected rotated position.

24. The rack of claim 23 wherein the tray-holder comprises an outwardly projecting knob on the tray and a detent on the first base, the detent being alignable with the knob to retain the tray in a rotated position.

25. A rack for holding a surgical suture, comprising:
a first base having a base connector that can releasably engage a mating base connector of a second base, and
a tray attached to the first base, said tray including a suture-holding section and a pin which defines a rotatable axis,
the first base comprising an upstanding tray connector that engages the pin for releasably connecting the tray to the first base.

26. A rack for holding a surgical suture, comprising:
a first base having a base connector that can releasably engage a mating base connector of a second base, and
a tray attached to the first base, said tray including a suture-holding section and a resilient clip for retaining a surgical suture in the suture-holding section.

27. The rack of claim 26 further comprising a suture-retaining boss.

28. A rack for holding a surgical suture, comprising:
a first base having a base connector that can releasably engage a mating base connector of a second base, and
a tray attached to the first base, said tray including a suture-holding section and a boss for engaging a corresponding recess in a suture package to retain said suture package in the suture-holding section.

29. A rack for holding a surgical suture, the rack comprising:
a first base having a base connector that can releasably engage a mating base connector of a second base,
a tray attached to the first base, said tray including a suture-holding section, and
a packaged suture positioned in the suture-holding section.

30. The rack of claim 29 further comprising multiple packaged sutures, said tray including multiple suture-holding sections, each of the multiple packaged sutures being located within a corresponding suture holding section.

31. A rack for holding a surgical suture, the rack comprising:
a first base having a base connector that can releasably engage a mating base connector of a second base,
a tray attached to the first base, said tray including a suture-holding section,
an unsealed packaged suture positioned in the suture-holding section, and
a sterile package surrounding said rack.

* * * * *